US007593556B2

(12) United States Patent (10) Patent No.: US 7,593,556 B2
Yasuda et al. (45) Date of Patent: Sep. 22, 2009

(54) SAMPLE PICTURE DATA PROCESSING METHOD AND SAMPLE INSPECTION SYSTEM AND METHOD

(75) Inventors: Nakahiro Yasuda, Chiba-ken (JP); Eric Benton, Chiba-ken (JP); Hitoshi Ishii, Kanagawa-ken (JP); Sumiko Takayama, Chiba-ken (JP); Shinsuke Inagaki, Chiba-ken (JP); Isao Kobayashi, Chiba-ken (JP); Atsushi Higashimata, Chiba-ken (JP); Yoshihiro Honma, Narashino (JP); Yosuke Umeshima, Chiba-ken (JP)

(73) Assignees: National Institute of Radiological Sciences (JP); SEIKO Precision Inc. (JP)

( * ) Notice: Subject to any disclaimer, the term of this patent is extended or adjusted under 35 U.S.C. 154(b) by 974 days.

(21) Appl. No.: 10/696,627

(22) Filed: Oct. 28, 2003

(65) Prior Publication Data

US 2007/0127842 A1 Jun. 7, 2007

(30) Foreign Application Priority Data

Oct. 29, 2002 (JP) ............................ 2002-314878
Oct. 29, 2002 (JP) ............................ 2002-314879

(51) Int. Cl.
*G06K 9/00* (2006.01)
(52) U.S. Cl. ..................................... 382/128
(58) Field of Classification Search ................. 382/100, 382/133, 128; 359/368, 362, 382; 396/432, 396/429, 548; 345/156, 157, 1.1, 1.2, 1.3, 345/2.1, 2.2, 4, 7, 9
See application file for complete search history.

(56) References Cited

U.S. PATENT DOCUMENTS 3,365,574 A * 1/1968 Duncumb .................. 250/310

(Continued)

FOREIGN PATENT DOCUMENTS

JP 64020449 1/1989

(Continued)

OTHER PUBLICATIONS

Leong F J et al: "Automated complete slide digitization: a medium for simultaneous viewing by multiple pathologists" Journal of Pathology, Chichester, Sussex, GB, vol. 195, No. 4, Nov. 2001, pp. 508-514, XP002246195 ISSN: 0022-3417.

(Continued)

*Primary Examiner*—Samir A. Ahmed
*Assistant Examiner*—Atiba O Fitzpatrick
(74) *Attorney, Agent, or Firm*—Adams & Wilks

(57) ABSTRACT

A sample inspection system has line sensors that generate sample picture data for layers of a sample disposed at different depths of the sample. The line sensors are arranged parallel to each other and displaced from each other in a vertical direction relative to the sample. A lens system focuses the layers of the sample at the different sample depths on the respective line sensors so that pictures of the layers at the different sample depths are read as line picture data by the line sensors. The sample inspection system includes an apparatus that stores the generated sample picture data, allows a planar region of the sample to be designated by a user for display, extracts picture data corresponding to the designated planar region for each of the sample layers from the sample picture data in response to designation of the planar region, and stores the extracted picture data as a set. An image processing apparatus displays on a display pictures corresponding to the extracted picture data of the respective layers by one of selectively displaying each picture individually in an alternating manner and simultaneously displaying two or more of the pictures together in a parallel or superposed manner.

3 Claims, 7 Drawing Sheets

X-AXIAL DIRECTION

U.S. PATENT DOCUMENTS

| | | | |
|---|---|---|---|
| 5,793,969 A * | 8/1998 | Kamentsky et al. | 709/213 |
| 6,028,306 A * | 2/2000 | Hayashi | 250/235 |
| 6,337,474 B1 * | 1/2002 | Morizono | 250/208.1 |
| 6,738,028 B2 * | 5/2004 | Asahi et al. | 345/1.1 |
| 2002/0044346 A1 * | 4/2002 | Nguyen et al. | 359/368 |

FOREIGN PATENT DOCUMENTS

| | | |
|---|---|---|
| JP | 03211682 | 9/1991 |
| JP | 04029036 | 1/1992 |
| JP | 04307028 | 10/1992 |
| JP | 10275150 | 10/1998 |
| JP | 2001242085 | 9/2001 |
| WO | 9913360 | 3/1999 |
| WO | 9930264 | 6/1999 |

OTHER PUBLICATIONS

Ferreira R et al: "The Virtual Microscope" AMIA Annual Symposium. A Conference of the American Medical Informatics Association. Proceedings. Proceedings of AMIA Annual Symposium the Emergence of Internetable Health Care Systems That Really Work, XX, XX, Oct. 25, 1997, pp. 449-453, XP002246194 * abstract; figures 2,3 * sections "Technical Challenges" and "System Design".

Razdan A et al: "Volume visualization of multicolor laser confocal microscope data" Computers and Graphics, Pergamon Press Ltd. Oxford, GB, vol. 25, No. 3, Jun. 2001, pp.371-382, XP004241647 ISSN: 0097-8493 abstract, sections 1.1.1, 1.1.2, figures 1-3, 5-7.

Kaufmann A et al: "Volume visualization in cell biolgoy" Proceedings of the Conference on Visualization. San Francisco, Oct. 23-26, 1990, Los Alamitos, IEEE Comp. Soc. Press, US, vol. Conf. 1, Oct. 23, 1990, pp. 160-168,471-472, XP010021074 ISBN: 0-8186-2083-8 * abstract; figures 3,4 * *p. 160, right-hand column, paragraph 2 * * p. 162, right-hand column, paragraphs 1-3 * pp. 165-166 section "Concluding Remarks".

* cited by examiner

X-AXIAL DIRECTION

SAMPLE PICTURE DATA PROCESSING METHOD AND SAMPLE INSPECTION SYSTEM AND METHOD

BACKGROUND OF THE INVENTION

1. Field of the Invention

The present invention relates to a sample picture processing method and a sample inspection system and method for sample picture data which have been obtained for a plurality of respective layers at different sample depths and with which a plurality of remotely-located personnel, such as expert departments at a hospital or university, can perform sample inspections of live cell, tissue, or the like in collaboration through a communication network.

2. Discussion of Related Art

In the laboratories of medical institutions such as hospitals, universities, and the like, inspection of cells, tissue, and the like is frequently performed using optical microscopes. In this regard, such inspection involves the magnification of an enormous number of cells in an inspection region having a very large area, the inspection of which requires a great deal of labor and imposes a heavy burden on personnel.

In the sample inspection of cells, tissue, or the like, therefore, such labor is typically divided between different departments in order to enhance the overall efficiency of the inspection process. Typically, an inspection department inspects for the existence or nonexistence of malignant cells with the microscope or the like. When a malignant cell has been detected, the inspection department obtains an image of the corresponding part of the sample and specifies it by marking or the like. A diagnosis department makes a medial diagnosis on the specified part. In addition, as means for joining the individual departments between which the labor is divided, a data transmission medium such as a telephone line or other public network, or a dedicated Internet line, has come into use in recent years, and a sample picture has been converted into data that may be exchanged between the respective departments through the data transmission medium.

The present inventors have previously proposed a way of converting sample pictures into data which uses as means for imaging cells, tissue, or the like magnified by a microscope, line pictures obtained by use of a line sensor, and for subjecting the line pictures to picture processing using a computer to promptly create a clear image of a very large region of the whole sample. Such means are disclosed in applicants' co-pending Japanese Patent Application Nos. 2002-097495, No. 2002-097497, No. 2002-097498, and No. 2002-097499.

In the inspection of samples comprised of cells, tissue, or the like, however, a cell cannot always be judged as being malignant or as being one for which a malignancy should be further considered, by observing only a fixed sample depth plane at a predetermined focal position. Such a judgment is often impossible unless the shape and configuration of the cell at different sample depths are observed. Therefore, for the purpose of performing a precise inspection of cells, tissue, or the like, it becomes important to change the focal position of a microscope to inspect the cells or the tissue in a multilevel fashion.

In this regard, with the inventions disclosed by the above-mentioned applications, a clear picture can be quickly obtained for a very large imaging region. However, a full-size picture cannot be entirely displayed on a display device such as a computer monitor because the image occupies a very large imaging region. In addition, where a plurality of pictures are prepared at different sample depths, the quantity of picture data is very large because each picture has a very large imaging region, and it has been difficult to promptly display the picture of the different sample depth.

When performing an inspection of cells or the like, detailed remarks of an inspection department that has inspected the cells or tissue are often required. As to any cell or cells for which it is determined that the presence of a malignancy should be further investigated, a picture with a changed sample depth or different magnification must often be obtained. In such case, a very exact and prompt sample inspection becomes possible if respective departments can exchange opinions and prearrange the refined conditions of re-imaging while watching the detailed picture imaged for the whole inspection region of a sample.

In this regard, using the inventions disclosed by the above-mentioned applications, a clear picture can be promptly created for the very large imaging region, but a full-sized version of the imaged picture cannot be displayed on a display device such as viewing monitor because the picture covers a very large inspection region. When the picture is reduced in size, the whole region can be displayed at one time by the display device, but the imaged cells or tissue cannot be clearly seen in the reduced picture, so that inspection and diagnosis are impossible. Besides, when the respective departments intend to exchange opinions and make arrangements while watching display devices such as monitors at different spots, only parts of the very large imaging region can be displayed on the display devices. Hence, the exact picture being displayed might differ among the remotely-located departments and a mistake can easily occur.

It is accordingly an object of the present invention to provide a sample picture data processing method and a sample inspection system which can promptly display the picture data of a plurality of layers of a sample each obtained at a different sample depth, and to provide a sample inspection method and a system therefor in which, merely by transmitting conditions of small data quantity, the predetermined planar region of a picture that has an imaging region larger than a region displayable by picture display means (such as a monitor) can be easily and promptly displayed at a plurality of spots.

SUMMARY OF THE INVENTION

In order to achieve the above objectives, the present invention provides a sample picture processing method and a sample inspection system and method for inspecting sample picture data for a plurality of respective layers at different sample depths and with which a plurality of remotely-located personnel can perform sample inspections of live cell, tissue, or the like in collaboration through a communication network A method for processing sample picture data in accordance with one aspect of the present invention comprises the steps of generating sample picture data for a plurality of layers each taken at a different sample depth from a sample through electronic imaging devices for the respective layers, storing the generated sample picture data, designating a planar region which is to be extracted from the respective sample picture data, extracting picture data corresponding to the planar region from the respective sample picture data for the respective layers upon receiving the designation of the planar region, and storing the extracted picture data for the designated planar region or for corresponding planar regions from all of the respective layers.

A sample inspection system according to another aspect of the present invention comprises means for generating sample picture data for a plurality of layers each at a different sample depth using electronic imaging devices for the respective layers, means for storing the generated sample picture data, means for designating a planar region which is to be extracted from the respective sample picture data, means for extracting picture data corresponding to the designated planar region from the respective sample picture data upon receiving the designation of the planar region, means for storing the extracted picture data, and a picture processing apparatus which displays extracted pictures of the respective layers on display means in an alternative way or simultaneously displays a combination of two or more of them, on the basis of the respective sample picture data and the respective extracted picture data of the respective layers.

Preferably, when the extracted picture for the designated region is to be displayed, a plurality of selected extracted pictures comprised of images of other layers of the sample from the same region are alternately displayable, or are displayable in parallel or superposition. In a preferred embodiment of the present invention, the electronic imaging devices are line sensors and the sample picture data consists of a set of individual line picture data obtained by the line sensors.

A sample inspection method in accordance with another aspect of the present invention comprises the steps of setting a first condition for designating a single layer image of a sample that is to be displayed on a specified terminal of a sample inspection system on the basis of pictures for each of a plurality of respective layers of the sample each taken at a different sample depth, setting a second condition for designating a predetermined planar region that is to be extracted from the single layer image designated by the first condition, displaying the predetermined planar region extracted from the single layer picture at the specified terminal in accordance with the first and second conditions, transmitting the first and second conditions to another terminal of the sample inspection system, and displaying an image of a planar region corresponding to the predetermined planar region at the other terminal in accordance with the first and second conditions that have been transmitted to the other terminal and on the basis of correspondent picture data that have been prestored at the other terminal in correspondence with the picture data.

Preferably, the sample inspection method further comprise an index display setting step of setting a third condition which represents an index for indicating a specified part of the predetermined planar region displayed at the specified terminal, a first index display step of displaying the index on the predetermined planar region displayed at the specified terminal, in accordance with the third condition, a second condition transmission step of transmitting the third condition to the other terminal, and a second index display step of displaying a correspondent index corresponding to the index at the other terminal in accordance with the third condition transmitted to the other terminal.

DETAILED DESCRIPTION OF THE PREFERRED EMBODIMENTS

Various preferred embodiments of the present invention will be described with reference to the attached drawings.

Figure 1:
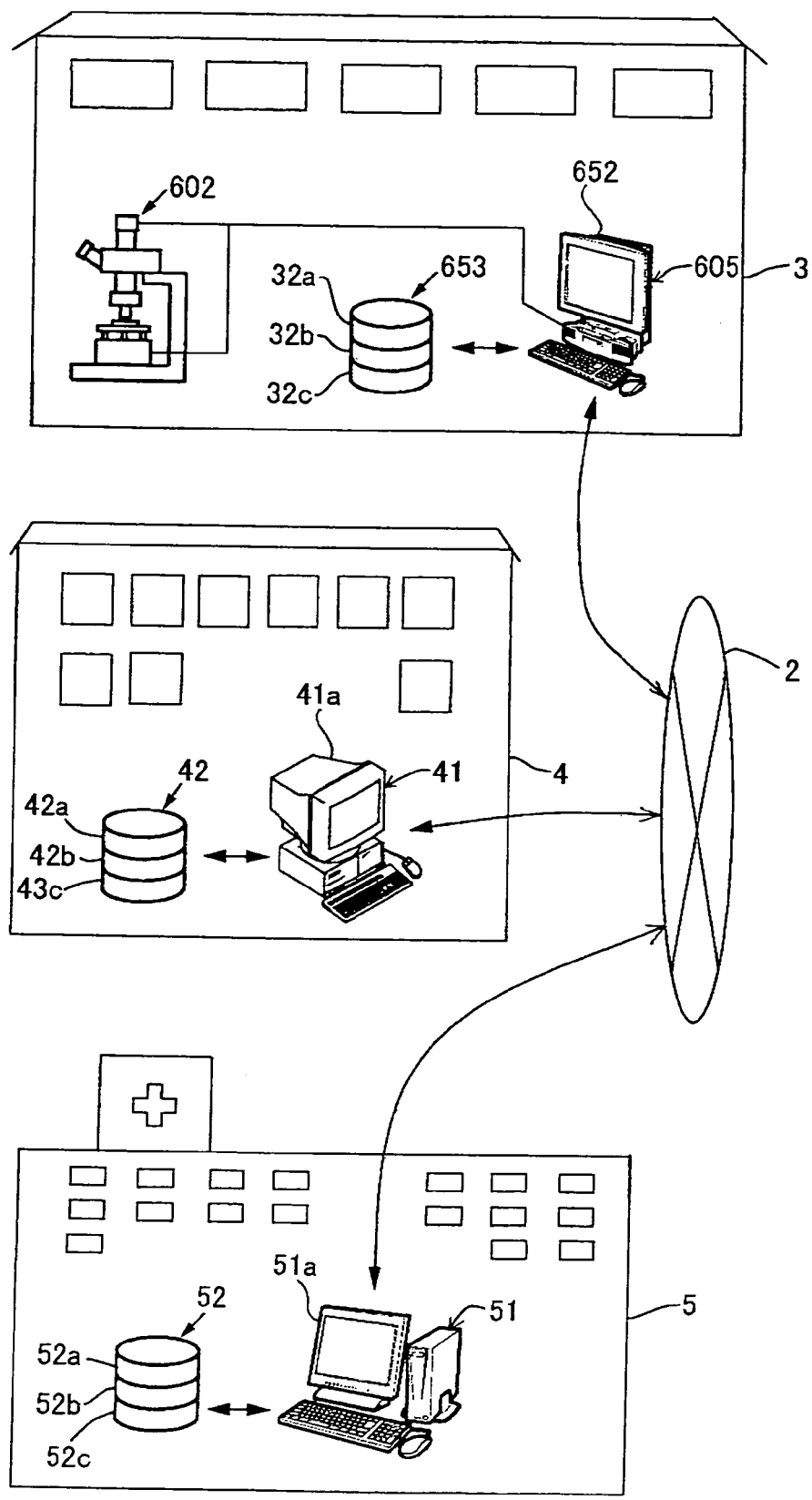
FIG. 1 is a general view of an inspection system according to the present invention.

Referring to FIG. 1, a sample inspection system known as a cytodiagnostic sample inspection system is shown. As illustrated, the system includes various remotely-located components that may preferably be arranged in different departments of a given facility. In the illustrated embodiment, the system includes a first terminal 605 located in a picture creation department 3, a second terminal 41 located in an inspection department 4, and a third terminal 51 located in a diagnosis department 5 of a hospital or university. Each of the first through third terminals is capable of transmitting and receiving data through a data transmission medium such as a telephone line or like line, or through a dedicated Internet line.

In the picture creation department 3, a sample comprising cells or tissue is magnified and imaged by a microscope apparatus 6 (shown in FIG. 3) to create a picture. In the inspection department 4, a malignant cell or any cells for which malignance should be further studied are specified from within the picture. In the diagnosis department 5, the specified cell or cells are diagnosed. Each of the terminals 605, 41, 51 include storage units 653, 42, 52, respectively, and the picture data 32*a*-32*c*, 42*a*-42*c*, 52*a*-52*c* of the cells or tissue imaged every three layers of different sample depths (focused positions) are respectively stored in the storage units. The term "sample depth" is used herein to indicate the difference in the focused position in the depthwise direction of the sample in the case where the sample is imaged by the microscope apparatus 6. That is, among the three layers mentioned above, the layer 32*a* is the uppermost layer which is nearest to an objective lens, the layer 32*c* is the lowermost layer which is furthest from the objective lens, and the layer 32*b* is an intermediate layer between the layer 32*a* and the layer 32*c*.

Figure 2:
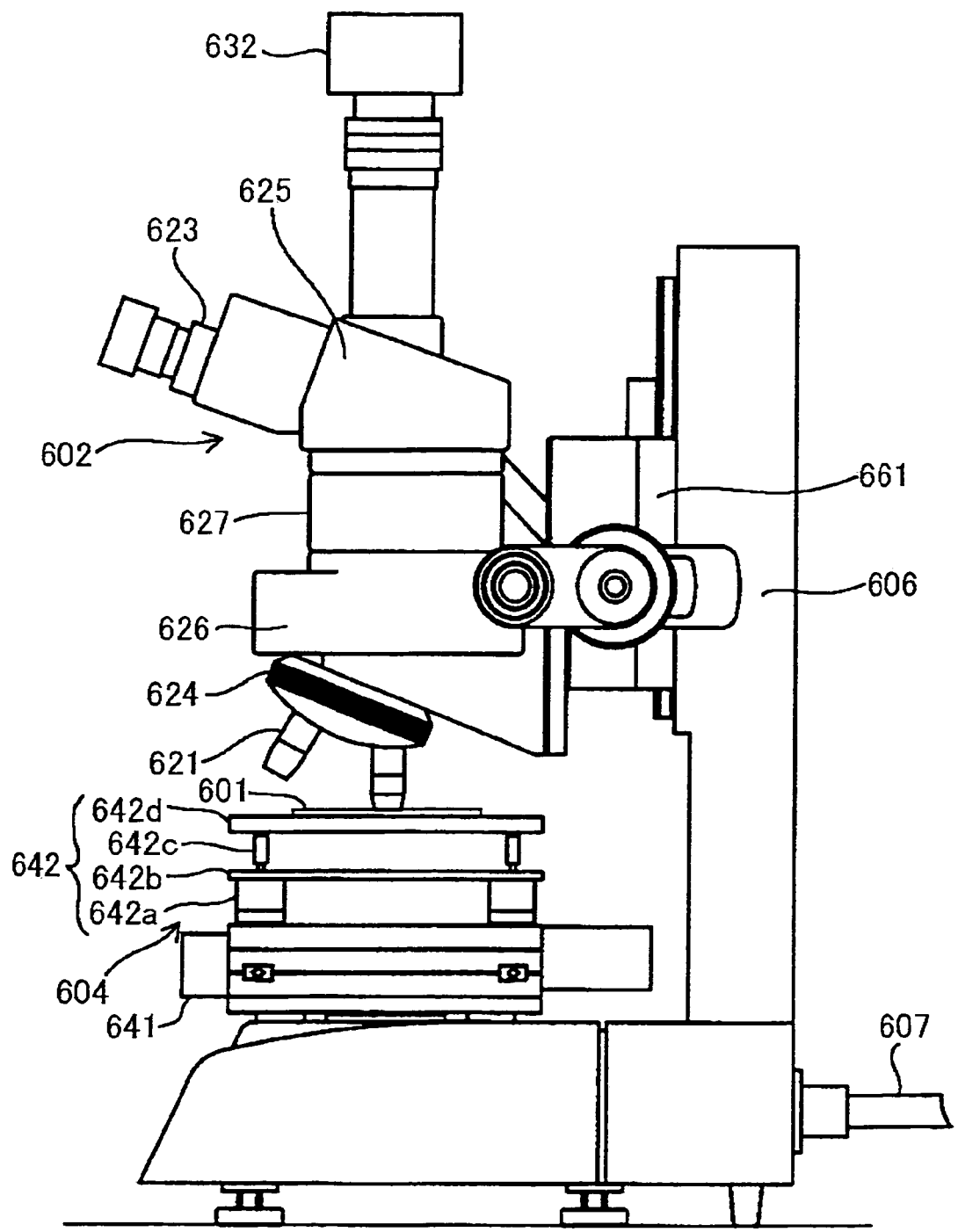
FIG. 2 is a view of a microscope apparatus.
Figure 3:
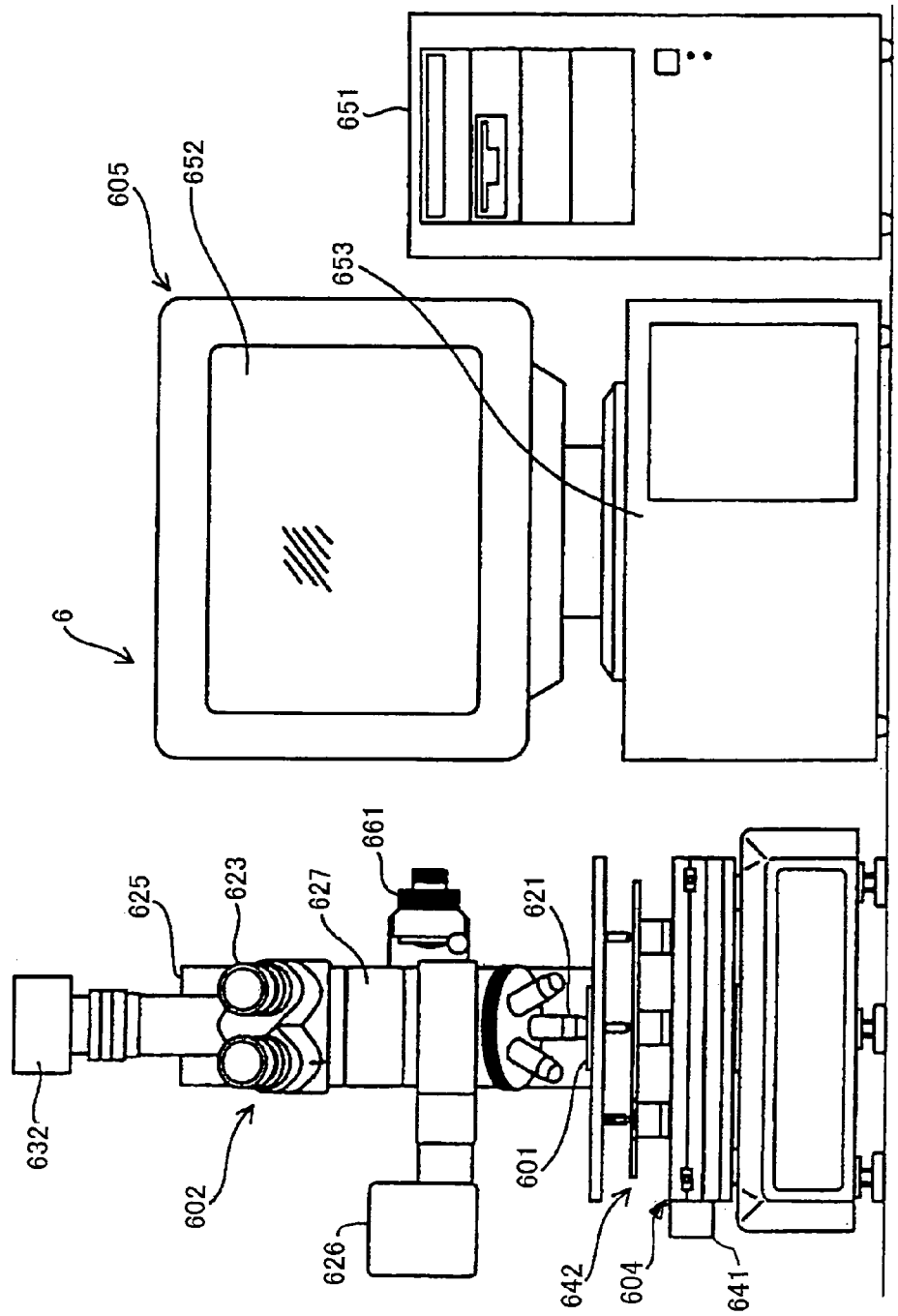
FIG. 3 is another view of a microscope apparatus.
Figure 4:
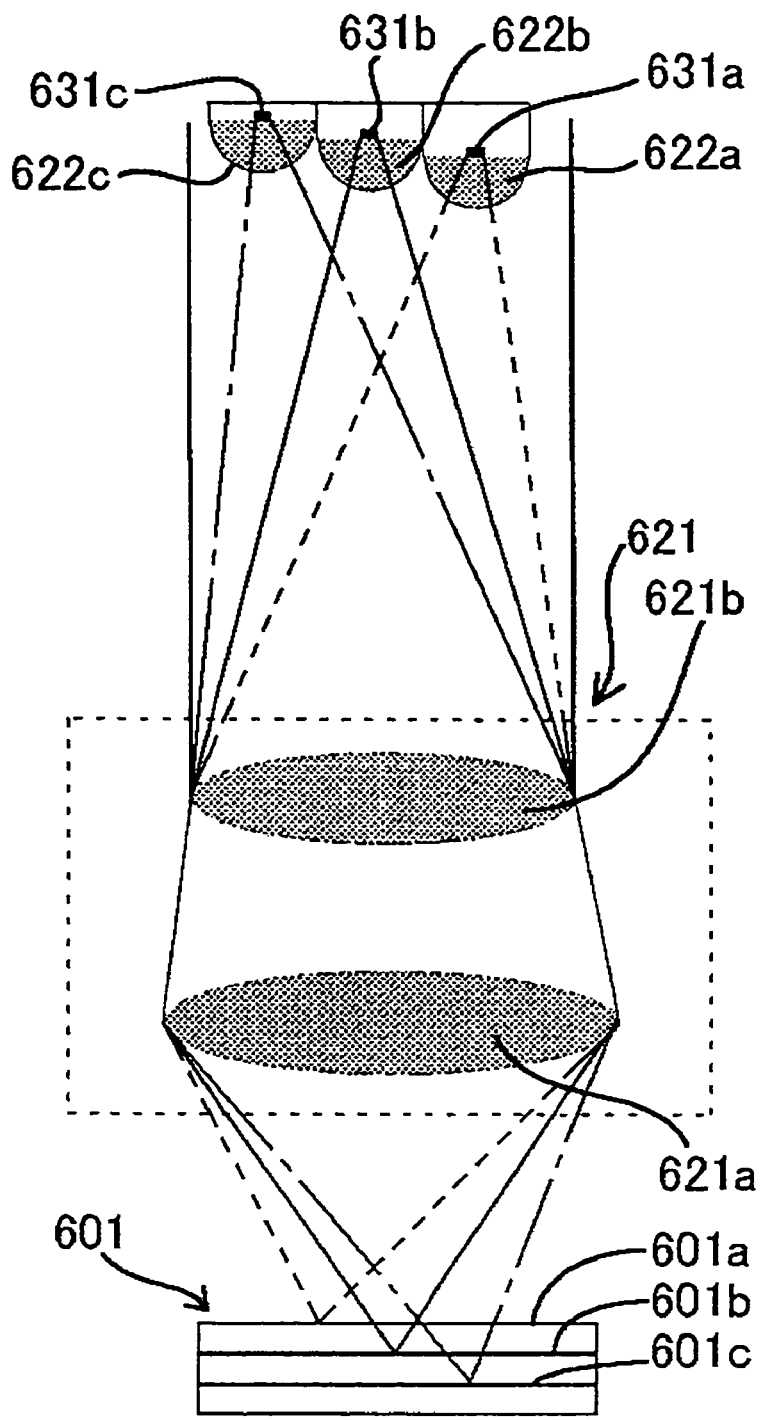
FIG. 4 is a layout diagram of optical lenses.

Next, the steps of creating the picture data of the cells or tissue in the picture creating department 3 will be described with reference to FIGS. 2-7. First, the steps of creating the picture data will be outlined. The three positions of the cells or tissue of a sample 601 at different sample depths are respectively and simultaneously focused on line sensors 631*a*, 631*b*, 631*c*, which are electronic imaging devices arranged in an array at different heights relative to the sample 601. In the presently described embodiment, the line sensors 631*a*, 631*b*, 631*c* are arranged stepwise, as shown in FIG. 4, to thereby make their heights different relative to the sample 601. In addition, pictures at the three different sample depths are read as line picture data by the three line sensors 631*a*, 631*b*, 631*c*. Additionally, the sample 601 is horizontally moved by movement means 604 shown in FIGS. 2-4, and the line picture data are successively stored in the storage unit 653 by the terminal 605 shown in FIG. 3. Subsequently, picture data of the sample 601 in the three layers of different sample depths is generated based on the recorded line pictures by an arithmetic processing unit 651 in a picture processing apparatus. The steps will be described in detail below.

First, the general construction of a microscope 602 will be described with reference to FIGS. 2 and 3. The microscope 602 which is used in the presently described embodiment of the present invention is an optical microscope. As will be appreciated by those of ordinary skill in the art, any other type of microscope may be used.

As commonly occurs in the inspection of cells, tissue, or like samples, a judgment of malignancy is difficult to make merely by viewing a focused part of the sample. Sometimes, it is necessary to take note of an unfocused and obscurely micrographed part of the sample (defocused part). When the sample is imaged by the optical microscope 602, the unfocused information is also stored as picture data, and hence, the imaging is suitable for the inspection of cells, tissue, or the like. The microscope 602 includes a body tube 625, an ocular lens for visual observation 623 attached to the body tube, a two-dimensional CCD sensor unit 627 which images some two-dimensional extent of the sample 601, and optical lenses which consist of objective lenses 621.

The body tube 625 is supported on an L-shaped frame 606 through a rack-and-pinion mechanism 661 which moves the body tube up and down. In order to illuminate the sample 601 from the rear surface thereof, an optical fiber 607 which introduces light from a halogen lamp (not shown) disposed outside is connected to the lower part of the L-shaped frame 606.

As shown in FIG. 4, the optical lenses are constructed of the objective lenses 621 each of which is made up of a composite lens formed of two lenses 621a, 621b, and three semi-cylindrical aberration compensation lenses 622a, 622b, 622c which are respectively disposed in correspondence with the three line sensors 631a, 631b, 631c arranged in parallel at the different heights. As indicated by broken lines, solid lines and dot-and-dash lines in FIG. 4, the aberration compensation lenses 622a, 622b, 622c lie at positions which are shifted from each other in an X-axis direction by the distances between the line sensors, and they are formed in such an optical configuration that layers (upper layer 601a, intermediate layer 601b, lower layer 601c) of the different sample depths are respectively focused on the line sensors 631a, 631b, 631c. Incidentally, three objective lenses 621 each having a different magnification are attached to a revolver 624, and they are manually switchable from one to another.

The three line sensors 631a, 631b, 631c and aberration compensation lenses 622a, 622b, 622c shown in FIG. 4 are accommodated in a camera body 632. As shown in FIG. 2, the camera body 632 is removably attached to the distal end of the body tube 625 of the microscope 602 using a standard F-mount lens mounting configuration of a single-lens reflex camera. Each of the line sensors 631a, 631b, 631c is constructed in such a way that charge coupled devices one latus of each of which is 7 µm long are rectilinearly arrayed in the number of 4000. Accordingly, in a case where imaging magnifications are 100, a range whose width is 7 µm/100=0.07 µm and whose length is 7 µm×4000/100=0.28 mm can be imaged at one time.

The horizontal portion of the L-shaped frame 606 is overlaid with the movement means 604. The movement means 604 includes a tilting table 642 on which the sample 601 is disposed, and a linear motor 641 which horizontally moves the tilting table rightwards and leftwards, and frontwards and rearwards. The linear motor 641 is a known type of motor which has an armature that moves on permanent magnets arranged in an array having the shape of a belt, and it is capable of high-speed drive, high response time, and high-precision positioning. As described below, the linear motor 641 is remote-controlled by a computer and moves the sample 601 to a predetermined position.

The tilting table 642 is constructed of three ultrasonic motors 642a which are arranged so as to form a regular triangle as viewed in plan, a flat table portion 642d which is supported at three points by the distal ends of the vertical output shafts 642c of the ultrasonic motors, and a fixation member 642b which fixes the mutual positions of the ultrasonic motors. The distal ends of the vertical output shafts 642c abut recesses formed in the rear surface of the table portion 642d so as to prevent their mutual horizontal positions from shifting.

Each of the ultrasonic motors 642a has a known structure in which an elastic member is disposed in contact with a piezoelectric ceramic material adapted to be deformed by applying a voltage thereto so that the elastic member generates bending vibrations in response to application of the voltage of an ultrasonic region to the piezoelectric ceramic to thereby rotate the output shaft. It is highly responsive and controllable, and it has the features of low operating sound, etc. In the ultrasonic motor 642a, the output shaft 642c has a threaded structure, and it is rotated to move up and down. In addition, the tilting table 642 adjusts the tilt of the sample 601 and a focal distance in accordance with instructions from the computer.

A halogen lamp (not shown) is accommodated in a lamp portion 626. Light from the halogen lamp is bent at right angles by a semitransparent mirror so as to extend along the optical axis of the microscope 602 so that the sample 601 is illuminated with light. Reflected light from the sample is intensified so as to obtain a clear picture. The lamp portion 626, which serves as a reflected light source, is used when the sample 601 is a substance having low light transmissivity. In addition, the optical fiber 607 introduces light from the halogen lamp (not shown) is configured as a transmitted light source outside the microscope apparatus and is connected to the lower part of the L-shaped frame 606 so that the sample 601 can also be illuminated from the rear surface thereof. The transmitted light source is often employed as a main light source when a sample of high light transmissivity, such as cells or tissue, is being observed. In the presently described embodiment, the sample 601 is illuminated from the rear surface thereof.

The two-dimensional CCD sensor unit 627 includes therein a two-dimensional CCD sensor (not shown) which is capable of obtaining an image within a two-dimensional range. More specifically, during cell inspection, it is sometimes necessary to display a picture enlarged by the microscope 602 directly on display means and to verify a specified part, range, or the like where a malignant cell exists while the display screen of the display means is being watched. Where only the line sensors 631a, 631b, 631c are disposed as imaging devices, the line picture which can be imaged at one time has a very small width. It is difficult to verify a specified part or range where a malignant cell exists while the displayed image having a narrow line width is being observed. In contrast, the two-dimensional CCD sensor is capable of imaging the sample with a wide two-dimensional range, so that is easy to verify the specified part or range of the cells, the tissue, or the like while the display screen based on the two-dimensional CCD sensor is being observed. The two-dimensional CCD sensor makes it possible to easily verify a specified part or range within the sample 601.

The two-dimensional CCD sensor is formed with charge coupled devices of the type which are used in a conventional CCD camera, each of which has a latus which is 21 µm long and which are arranged in plan view in a matrix of 600 in a longitudinal direction and 600 in a lateral direction, so that over 350,000 charge coupled devices are included. The CCD sensor images the predetermined range of the sample 601 through the semitransparent mirror.

A commercially available computer such as a "personal computer" is used as the terminal 605 and is comprised of the arithmetic processing unit 651, the display means 652, and the storage unit 653 for storing the line picture data therein. The arithmetic processing unit 651 is disposed in the picture processing apparatus and, as described below, executes the setting of the imaging region of the sample 601, the movement of the movement means 604, the instruction of the execution of imaging by the line sensors 631a, 631b, 631c which is based on a movement magnitude fed back from the encoder of this movement means, the acceptance of the line picture data imaged by the line sensors, and the synthesis of the line picture data for the creation of the general planar picture of the imaging region.

Figure 7:
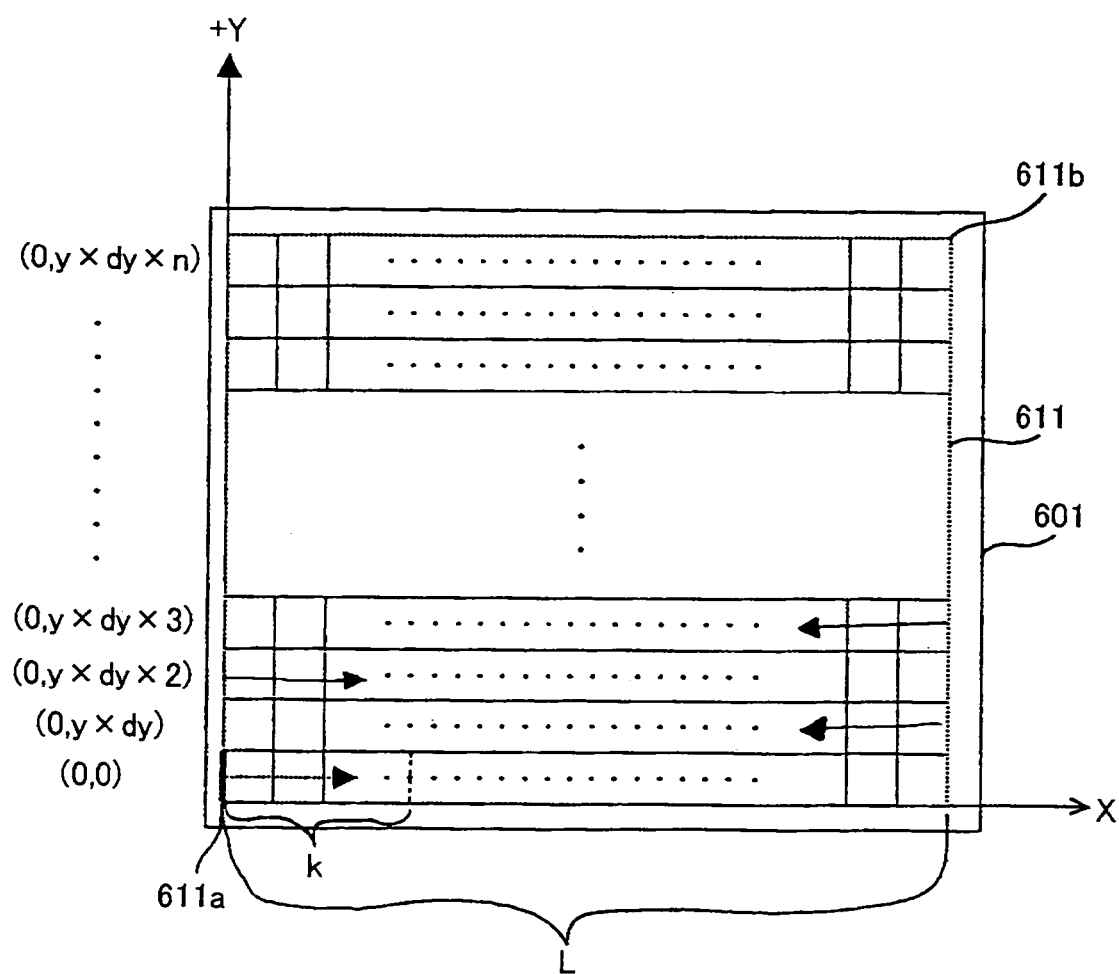
FIG. 7 is an explanatory diagram of the imaging steps of line pictures.

Next, there will be described the steps of creating the picture data 32a-32c of the cells or tissue by the constituent components stated above. First, as shown in FIG. 2, a sample 601 in which a cell or tissue piece to be inspected is interposed between a slide glass and a cover glass and set on the upper surface of the table portion 642d of the tilting table 642. The sample is fixed by suction to the table portion 642d through vacuum means, or the like, so as not move. Subsequently, as shown in FIG. 7, the inspection region 611 of the sample 601 is set by an input from the input means of the personal computer.

Herein, the inspection region 611 is set for setting the start point 611a and end point 611b of the imaging of the line pictures successively imaged by the line sensors 631a, 631b, 631c, as will be described below. Incidentally, an imaged picture having some two-dimensional extent is required for the setting of the inspection region 611. Therefore, the setting is performed by displaying imaging data from the two-dimensional CCD sensor, on the display means 652 of the terminal 605, and then moving and adjusting the movement means 604 in X- and Y-directions while the display screen of the display means is being viewed. Thus, the XY-coordinates of the positions 611a, 611b on a diagonal line are stored in the arithmetic processing unit 651 as information items which correspond to the movement start point and end point positions of the linear motor 641 of the movement means 604. As described below, accordingly, in the case of imaging the sample by the line sensors 631a, 631b, 631c, the linear motor 641 is sequentially moved from the inner side position 611a being the first imaging position, to the horizontal direction position 611b being the last imaging position, in accordance with instructions from the arithmetic processing unit 651.

In setting the inspection region 611, adjustment of the focal distance of the sample 601 and the tilt are simultaneously performed. More specifically, in setting the inspection region 611, the two-dimensional CCD sensor is first focused on the upper layer 601a of the sample 601 at the start point position 611a while a display picture from this two-dimensional CCD sensor as indicated on the display means 652 is being watched. Subsequently, the linear motor 641 is moved in the X-axis direction, and the two-dimensional CCD sensor is focused at the right end part position of the inspection region 611. Besides, a tilt in the X-axis direction is calculated from the deviation between the focused positions, and the tilt of the tilting table 642 is adjusted. Thereafter, using similar means, the two-dimensional CCD sensor is focused at the right upper part position 611b of the inspection region 611, and a tilt in a Y-axis direction is adjusted.

When the microscope apparatus is so constructed that the focal position of the two-dimensional CCD sensor coincides with the focal position of the line sensor 631a for imaging the upper layer 601a of the sample 601, the line sensor 631a can be immediately focused on the upper layer 601a of the sample. The aberration compensation lenses 622a, 622b, 622c are designed so that the other line sensors 631b, 631c may be focused on the positions of their respective focal depths simultaneously with the line sensor 631a. Therefore, at the stage at which the two-dimensional CCD sensor has been focused, all of the three line sensors are focused.

Subsequently, the steps of imaging the sample 601 by the line sensors 631a, 631b, 631c will be described with reference to FIGS. 7 and 8. The imaging is controlled by a program built into the arithmetic processing unit 651. First of all, the arithmetic processing unit 651 sets an inspection position of j=0 and k=0 by the encoder and recognizes the inspection position as coordinates of X=0 and Y=0. In addition, the arithmetic processing unit 651 causes the sample 601 to move to the XY-coordinate (0, 0) position by the linear motor 641. The XY-coordinate (0, 0) position is the left lower corner 611a of the inspection region 611 shown in FIG. 7, and this point becomes the start point at which the imaging is started. The point becomes the position of (a) in FIG. 8, and the line sensor 631a is arranged at the position at which it overlies the left lower corner 611a.

Figure 8:
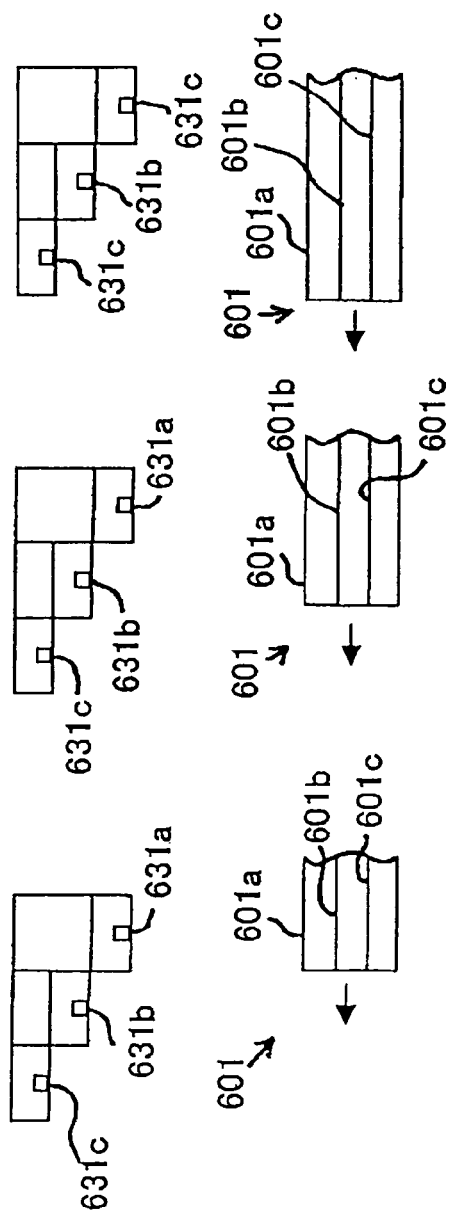
FIG. 8 is an explanatory diagram concerning the imaging of the line sensors.
Figure 8:
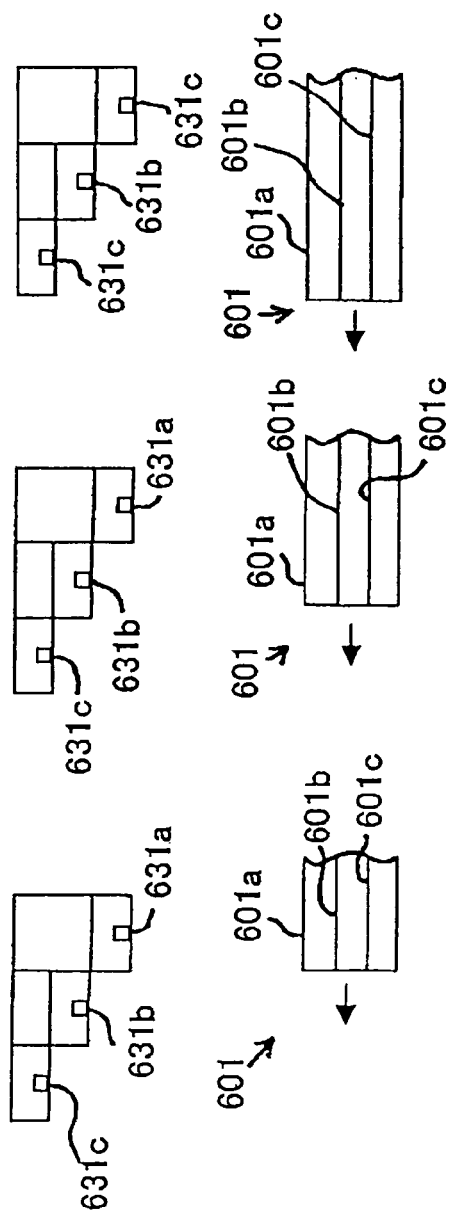
Figure 8:
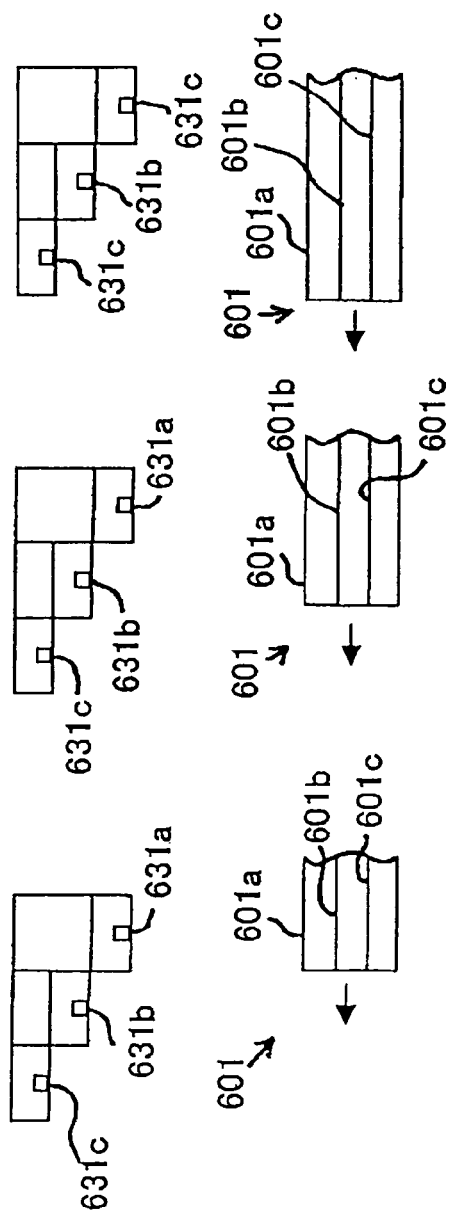
Figure 8:
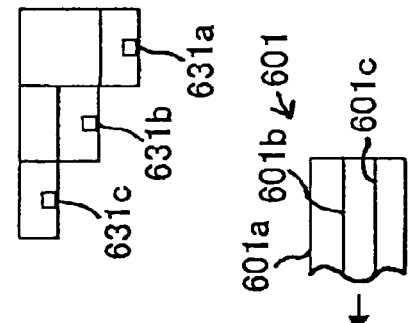
Figure 8:
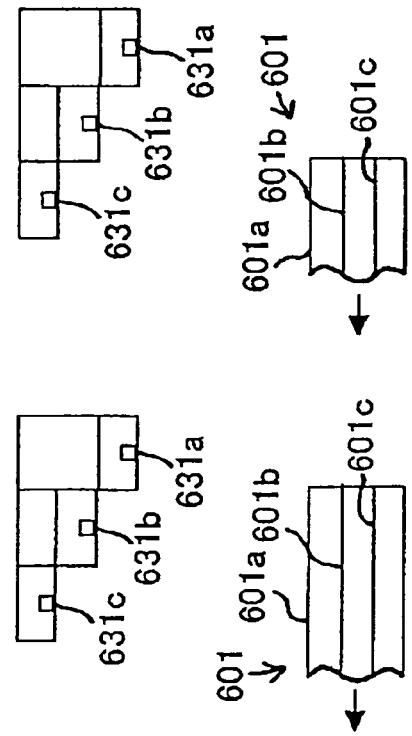
Figure 8:
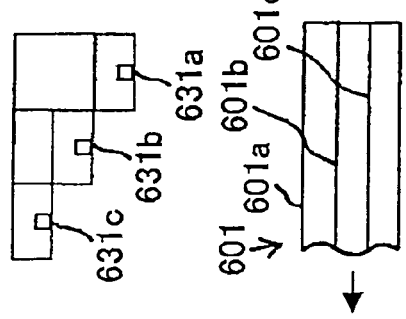

When the start point of the imaging position has been set at the position of the left lower corner 611a of the inspection region 611, the arithmetic processing unit 651 sets a movement magnitude dx for the X-axis, and it stores in the storage unit 653 respective line pictures imaged by the line sensors 631a, 631b, 631c at the inspection position (0, 0) and starts the movement of the linear motor 641 in the X-axis direction at a constant rate ((a)-(c) in FIG. 8). The movement magnitudes of the movement means 604 are measured by the encoder, and the data thereof is sent to the arithmetic processing unit 651. When it is judged by the arithmetic processing unit 651 that the inspection region 611 has been moved one measurement width component of the line sensors 631a, 631b, 631c in the X-axis direction by the movement means 604, the arithmetic processing unit 651 stores in the storage unit 653 line pictures from the line sensors at the second inspection position of X=1dx and Y=0, namely, coordinates (1dx, 0).

The arithmetic processing unit 651 adds "1" to k each time the pictures of one line have been recorded. It stores the line pictures in the storage unit 653 sequentially for the range of one row having an X-axis direction length L until the linear motor 642 moves in the X-axis direction at a constant rate to bring the inspection position to the right lower corner of the inspection region 611 shown in FIG. 7 (in correspondence with the movements at (d)-(f) in FIG. 8).

Meanwhile, when the acceptance of the imaging of the lowermost stage of the inspection region 611, namely, Y-axis coordinate=0, has been completed, the arithmetic processing unit 651 sets j=1 for the encoder and moves the inspection position to the inspection position of X=L and Y=1dy, namely, the position of XY-coordinates (L, 1dy) by the linear motor 641. This position is a position which lies on the right of the left lower corner 611a of the inspection region 611 shown in FIG. 7, by L in the X-axial direction, and which is shifted in the Y-axial direction in correspondence with the length of the line sensors 631a, 631b, 631c. At the position of Y=1dy, line pictures are accepted sequentially from the right end to the left end of the inspection region 611.

In the foregoing manner, while the scanning direction of the line sensors 631a, 631b, 631c is being altered leftward or rightward, the arithmetic processing unit 651 sequentially records line pictures in the storage unit 653 together with measured coordinates the moment the line sensors 631a, 631b, 631c have moved into a new imaging range. Meantime, when J>n has been reached, the arithmetic processing unit 651 judges that the whole inspection region 611 has been imaged, and it synthesizes the recorded line pictures and stores the planar picture data of the whole inspection region in the layers 601a, 601b, 601c of the three different sample depths as the layer picture data 32a, 32b, 32c in the storage unit 653, respectively.

In the imaging performed by the line sensors 631a, 631b, 631c, the arithmetic processing unit 651 affixes the XY-coordinates and the sample depths, namely, Z-axis coordinates in the above inspection region 611, to the individual imaged line picture data. More specifically, as shown in FIG. 4, the layers 601a, 601b, 601c of the different sample depths are simultaneously imaged by the respective line sensors 631a, 631b, 631c and are shifted the distances between the devices of the line sensors from each other in the X-axial direction. Regarding the magnitude of the shift, with respect to the line picture which is imaged by the line sensor 631a, the shift magnitude is added to the X-value of the coordinates of the line picture which is imaged by the line sensor 631b, and the X-coordinate value shifted the distance between the devices is affixed. Further, the X-value of the coordinates of the line picture which is imaged by the line sensor 631c is shifted the distance between the devices still more, and the shifted value is affixed. Besides, the layers 601a, 601b, 601c are shifted the mounting heights of the line sensors from each other in a Z-axial direction. Regarding the magnitude of the shift, with respect to the line picture which is imaged by the line sensor 631a, the shift magnitude is added to the Z-value of the coordinates of the line picture which is imaged by the line sensor 631b, and the Z-coordinate value shifted the mounting height is affixed. Further, the Z-value of the coordinates of the line picture which is imaged by the line sensor 631c is shifted the mounting height still more, and the shifted value is affixed. In this manner, in imaging the individual line pictures, the XYZ-coordinates of the imaging positions in the whole inspection region 611 of the sample 601 are affixed to the line picture data by the arithmetic processing unit 651 of the terminal 605.

With respect to the manner of imaging performed by the line sensors 631a-631c, all the line sensors may be always held in their imaging states as explained above. Alternatively, the imaging may be controlled by the arithmetic processing unit 651 so that, at one end part of the sample (corresponding to (a)-(c) in FIG. 8), only the line sensor 631c may be used for the imaging in FIG. 8(a), the line sensors 631c and 631b being used for the imaging in FIG. 8(b), all the line sensors being used for the imaging in FIG. 8(c) and thereafter, and that, at the other end part of the sample (corresponding to (d)-(f) in FIG. 8), all the line sensors may be used for the imaging until the stage of FIG. 8(d) is reached, in which the line sensors 631b and 631a are used for the imaging in FIG. 8(e) and only the line sensor 631a is used for the imaging in FIG. 8(f). That is, when the control is performed in this manner so that the line sensor to image a position where the sample does not exist may not be used for the imaging, the imaging data of places where the sample does not exist can be removed from the picture data.

Next, there will be described a method of displaying the picture data 32a-32c of the whole inspection region on the display means 652. First, a layer picture to be displayed at the terminal 605 is selected, such as, for example, the layer picture 32a. The arithmetic processing unit 651 of the terminal 605 displays a thumbnail (reduced picture) of the whole region of the selected layer picture 32a on the display means 652. When a desired planar region to display a non-reduced picture is designated on the thumbnail, the arithmetic processing unit 651 selects the layer picture data 32a from among the picture data stored in the storage unit 653 and extracts picture data corresponding to the designated planar region from among the selected layer picture data. The arithmetic processing unit 651 also extracts picture data corresponding to planar regions at positions corresponding to the designated planar region from among the other layer picture data 32b, 32c. Subsequently, the arithmetic processing unit 651 brings the picture data of the respective planar regions extracted from among the corresponding layer picture data 32a-32c into one set, and then stores them in a picture saving memory disposed in the picture processing apparatus. Thereafter, the arithmetic processing unit 651 displays the picture of the designated planar region of the selected layer picture 32a on the display means 652.

In the foregoing manner, the arithmetic processing unit 651 extracts the respective layer picture data corresponding to the planar region displayed on the display means 652 and stores them in the picture saving memory separately. Therefore, when an operator having watched the displayed layer picture wants to view an unfocused and obscurely micrographed part and the other layer pictures of sample depths focused at the positions different from the position of the displayed layer picture, the other layer pictures can be displayed on the display device 652 without expending a long time by using the picture data separately stored in the picture saving memory. Consequently, the operator can display the pictures of any designated planar region on the display means 652 by using only the terminal 605, as if he/she were observing the sample depths of the three focal positions while looking into the ocular lens 623 of the microscope 602. That is, the arithmetic processing unit 651 separately stores the respective layer picture data corresponding to the extracted planar regions, whereby visual fields virtually viewed by the microscope can be reproduced only by the terminal 605.

Figure 5:
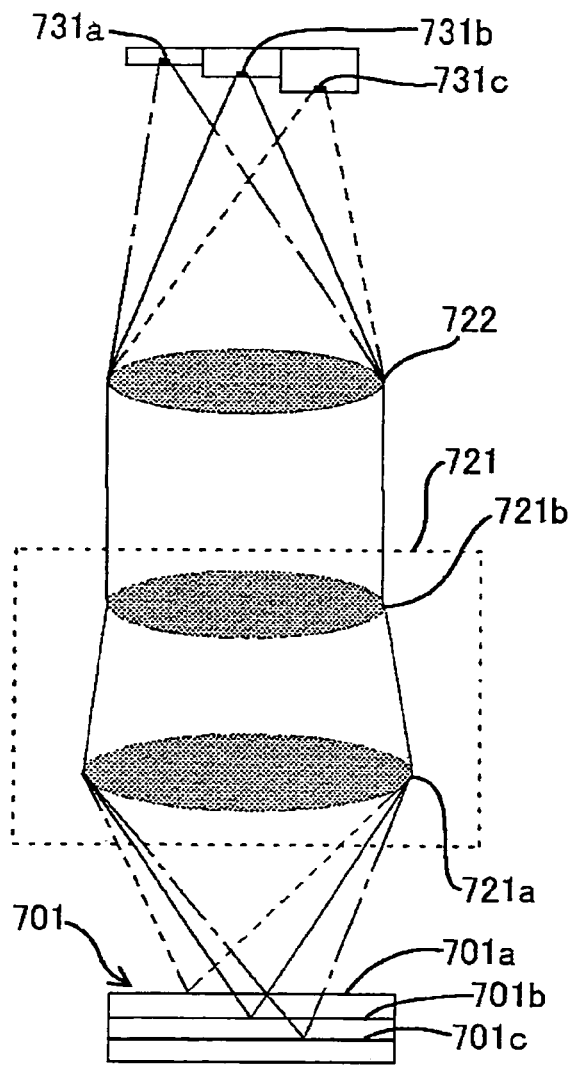
FIG. 5 is another layout diagram of optical lenses.
Figure 6:
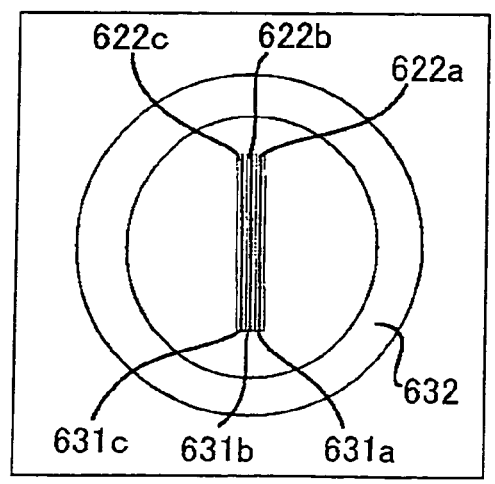
FIG. 6 is an enlarged front view of line sensors and aberration compensation lenses.

The optical layout is not restricted to the case where the aberration compensation lenses 622a, 622b, 622c are respectively disposed for the line sensors 631a, 631b, 631c as shown in FIG. 4, but line sensors 731a, 731b, 731c may instead be respectively focused on layers 701a, 701b, 701c of different sample depths by an aberration compensation lens 722 having a plurality of (three in the illustrated embodiment) radii of curvature, as shown in FIG. 5. Besides, the construction of each of the line sensors 631a, etc. is not restricted to the case where the CCDs numbering 4000 are arrayed in one row, but more or less CCDs may be arrayed in several rows. In addition, regarding the size of each individual CCD which constitutes the line sensors 631a, 631b, 631c, smaller. CCDs can obtain an image of higher resolution. In case of using CCDs of larger sizes, however, a picture of higher resolution can be obtained by enlarging the magnifications of the imaging.

Apart from the manual operations described before, adjustment of the focal positions and tilt of the sample 601 can be easily automated in such a way that focusing means having laser beam projection means is incorporated into the microscope 602, and that the tilting table 642 is moved on the basis of instructions from the computer. Further, the number of the line sensors 631a, 631b, 631c is not restricted to three as described above, but it can be set at two or at four or more. The inspection regions of sample depths corresponding to each number can be simultaneously imaged.

Next, a cell inspection system will be described. First, the arithmetic processing unit 651 stores the picture data 32a-32c of the whole inspection regions in the layers 601a, 601b, 601c of the three sample depths to be stored in the storage unit 653, respectively, in the storage unit 653 of the picture creating department 3, and it also records them in a DVD which is a large-capacity record medium. Besides, such DVDs are forwarded to the inspection department 4 and the diagnosis department 5, and the picture data are respectively stored in the storage units 42, 52 through the terminals 41, 51. Thus, the same picture data 42a-42c, 52a-52c of the whole inspection regions in the layers 601a, 601b, 601c of the different sample depths are also existent in the terminals 41, 51 of the inspection department 4 and the diagnosis department 5 in relation to the cells or tissues to-be-inspected.

The reason why the storage units 653, 42, 52 are included in the respective departments so as to record the picture data of the whole imaging regions of the cells or tissues is that the picture data become an enormous capacity of about 1 Gbyte or more for every sample. There is also considered a system wherein the picture data are recorded in a single common server or the like beforehand, and wherein the recorded data are, for example, accessed or downloaded from the terminals of the respective departments by utilizing data transmission media. However, since the picture data capacity is excessively large, an excessively long time is expended on transmission/reception with the present-day transmission speed, and the system is unsuitable for practical use.

In the inspection department 4, therefore, the picture of the predetermined planar region of a desired layer among the three layers of the cells or tissues is first displayed at the terminal 41 on the basis of the picture data 42a-42c stored in the storage unit 42, and the existence or nonexistence of any malignant cell or any cell for which malignance ought to be considered is inspected. The picture data 42a-42c are the picture data of an area which is larger than an area displayable by display means 41a being the first picture display means of the terminal 41. In order to display the picture data at the terminal 41, therefore, the predetermined planar region to be displayed is designated from the picture data of the desired layer.

In determining the existence of a malignant cell or a cell for which malignance should be further considered, the range thereof is specified on a display screen. Specifying methods include one in which a cell is demarcated by a frame line or coloring on the display screen, and one in which an arrow or sign and/or comments are inserted into a displayed picture.

In a case where the inspection is to be simultaneously performed by each of the different departments, the inspection department 4, diagnosis department 5 and picture creating department 3 are first brought into communicable states through a data transmission medium such as a telephone line or like public line, or a dedicated Internet line. The operator of the inspection department 4 operates the terminal 41, and selects a layer picture to be displayed at the terminal 41, for example, the layer picture 42a. The terminal 41 sets sample depth information for designating the selected layer picture, as a first condition. In addition, the terminal 41 displays the thumbnail (reduced picture) of the whole set layer picture 42a on the display means 41a.

The operator selects a desired planar region to display a non-reduced picture from within the thumbnail. The terminal 41 sets coordinate information and the like for designating the selected planar region, as a second condition. The arithmetic processing unit of the terminal 41 extracts picture data which correspond to planar regions at positions corresponding to the designated planar region from the other layer picture data 42b, 42c. Subsequently, the arithmetic processing unit brings the picture data of the respective planar regions extracted from among the corresponding layer picture data 42a-42c into one set, and then stores them in a picture saving memory disposed in a picture processing apparatus. Thereafter, using the first condition and the second condition, the terminal 41 selects the layer picture data 42a from among the picture data stored in the storage unit 42 and then extracts picture data corresponding to the selected planar region, from within the layer picture data 42a, and it displays the picture of the selected planar region on the display means 41a. The first condition and the second condition have a very small data quantity unlike the layer picture data of the selected planar region, so that a long time is not expended on communications even when the conditions are transmitted/received by the data transmission medium.

At the same time, the terminal 41 transmits the first condition and the second condition to the terminals 605, 51 of the picture creating department 3 and the diagnosis department 5 through the data transmission medium through the communication means. Using the first and second conditions received, the terminals 605, 51 select the layer picture data 32a, 52a from the corresponding picture data stored in the storage units 653, 52, extract picture data corresponding to the selected planar regions from within the selected layer picture data, and display pictures corresponding to the picture displayed at the terminal 41 on display means 652, 51a comprising second picture display means. Of course, in the same manner as at the terminal 41, the respective arithmetic processing units of the terminals 605, 51 extract picture data which correspond to planar regions at positions corresponding to the designated planar region from within the other layer picture data 32b, 32c and 52b, 52c. The respective arithmetic processing units bring the picture data of the planar regions extracted from within the layer picture data 32a-32c and 52a-52c into individual sets, and they store the picture data in picture saving memories disposed in the picture processing apparatuses.

As a result, the same picture is displayed at the terminal 41 of the inspection department 4, the terminal 605 of the picture creating department 3 and the terminal 51 of the diagnosis department 5 merely by transmitting/receiving the first and second conditions through the data transmission medium.

When the operator of the inspection department 4 indicates an index for the demarcation based on the frame line or coloring, or for inserting the arrow or sign or comments into the displayed picture, on the picture displayed at the terminal 41 from an input device such as mouse or keyboard, the terminal 41 sets information representative of the sort, coordinates, etc., of the index, as a third condition. Likewise to the first and second conditions, the third condition has a small data quantity as compared with the layer picture data of the selected planar region, and a long time is not expended on the communications thereof. At the same time, the terminal 41 transmits the third condition to the terminal 605 of the picture creating department 3 and the terminal 51 of the diagnosis department 5 through the data transmission medium by the transmission means. Using the third condition received, the terminals 605, 51 display indices on the display means 652, 51a. Consequently, the indices which correspond to the index displayed at the terminal 41 are displayed also on the display means 652, 51a of the terminals 605, 51.

Accordingly, it is possible to study the same planar region within a picture having a very large imaging region in such a way that the inspection department 4, the picture creating department 3 and the diagnosis department 5 merely transmit/receive small data quantities of the first-third conditions through the data transmission medium. By way of example, the labor of searching for any malignant cell is not required in the diagnosis department 5. Besides, in a case where, apart from the malignant cell or the cell for which the malignance ought to be considered as has been specified in the inspection department 4, any other cell for which malignance ought to be considered has been found out in the diagnosis department 5, or where imaging data of still higher magnifications, for example, are required, the operator of the diagnosis department 5 specifies a corresponding position on the display screen of the terminal 51 or appends the instruction of an imaging condition. Then, in the same manner as already described in relation to the terminal 41, the terminal 51 transmits the first-third conditions to the terminals 605, 41 of the inspection department 4 and picture creating department 3 through the data transmission medium, and the specified range, the imaging condition, etc. are immediately displayed. Processing can be quickly and appropriately executed in accordance with the displayed instructions.

Besides, in a case, for example, where the operator of the inspection department 4 cannot form a judgment on the malignant cell with only the focused part of a picture currently under display, and where he/she wants to watch a defocused part out of focus, with a focused layer picture of different sample depth, he/she designates the focused picture of the layer of different sample depth at the terminal 41. Then, since the picture data of the other layers corresponding to the displayed planar region are stored in the picture saving memory, the arithmetic processing unit of the terminal 41 can immediately display the different layer picture merely by altering the first condition and without the necessity of extracting the corresponding planar region from the whole imaging region anew. That is, in a case, for example, where the operator wants to change-over the display from the layer picture 42a currently under display to the layer picture 42b, he/she selects the layer picture 42b. Then, the terminal 41 resets sample depth information for designating the selected layer picture, as the first condition, and it displays the extracted layer picture 42b of the picture saving memory on the display means 41a. Besides, the terminal 41 merely transmits only the altered first condition to the other terminals 605, 51, whereby the same altered layer picture as at the terminal 41 is extracted from the picture saving memories and immediately displayed at the other terminals.

In the above embodiment, studies have been made in the three departments while the same picture is being simultaneously watched. However, the present invention is not restricted to this aspect, but studies may well be similarly made in only two departments or in four or more departments while the same picture is being watched. Since, in this manner, information and opinions can be exchanged through the data transmission medium, it is permitted to efficiently perform a very exact sample inspection as if the members of the departments met together. Besides, the present invention is not limited only to the cells or the tissues, but it can be utilized for the sample inspection of blood, bacteria, or the like. In addition, the above embodiment is so constructed that the extracted picture of each layer is displayed on the display means 652 in an alternative way, but the combination of a plurality of extracted pictures of the respective layers may well be simultaneously displayed on the display means 652 without being restricted to the construction. By way of example, extracted pictures of two or more sample depths may well be disposed in superposition, or two or more extracted pictures may well be displayed on the display means 652 in parallel. In this case, the two or more pictures can be displayed on the display means in parallel by making each planar region half the size of the screen or smaller. In this way, the inspection is facilitated more owing to easier multilevel recognition because the two or more pictures are displayed on the display means 652. Besides, the number of the line sensors of the microscope apparatus is not restricted to three, but a single line sensor or four or more line sensors may well be employed.

The picture data of a plurality of layers of different sample depths can be promptly displayed on display means. Moreover, when a plurality of pictures are displayed in parallel or in superposition, it is facilitated to recognize cells or the likes in multilevel fashion. Moreover, the predetermined planar region of a picture having a very large imaging region can be easily and promptly displayed at a plurality of spots merely by transmitting the conditions of small data quantities.

What is claimed is:

1. A sample inspection system comprising:
   imaging means for generating sample picture data for a plurality of layers of a sample each having a different sample depth, the imaging means comprising a plurality of line sensors arranged parallel to one another, spaced-apart from each other in a horizontal direction, and displaced from each other in a vertical direction relative to the sample;
   a lens system having an optical configuration that focuses the layers of the sample at the different sample depths on the respective line sensors so that pictures of the layers at the different sample depths are read as line picture data by the line sensors;
   means for storing the sample picture data generated by the imaging means;
   means for designating a planar region which is to be extracted from the respective sample picture data;
   means for extracting picture data corresponding to reduced pictures of the entire designated planar region for each of the respective layers from the respective sample picture data in response to designation of the planar region, and for storing the extracted picture data as a set; and
   a picture processing apparatus that displays on a display pictures corresponding to the extracted picture data of the respective layers by one of selectively displaying each picture individually in an alternating manner and simultaneously displaying two or more of the pictures together in a parallel or superposed manner, and that displays on the display information corresponding to an index for demarcation on the displayed pictures.

2. A sample inspection system according to claim 1; wherein the line sensors are incorporated in an optical microscope and are arranged for simultaneously obtaining images of the sample layers at different sample depths.

3. A sample inspection system according to claim 1; wherein the lens system comprises a plurality of objective lenses common to all of the line sensors and a plurality of semi-cylindrical aberration compensation lenses disposed in correspondence with the respective line sensors.

* * * * *